United States Patent [19]

Suzuki et al.

[11] 4,245,078

[45] Jan. 13, 1981

[54] PROCESS FOR PRODUCING TEREPHTHALIC ACID

[75] Inventors: Takashi Suzuki, Niigata; Akira Tateishi, Toyosaka; Susumu Naito, Niigata, all of Japan

[73] Assignee: Mitsubishi Gas Chemical Company, Inc., Tokyo, Japan

[21] Appl. No.: 719,453

[22] Filed: Sep. 1, 1976

[30] Foreign Application Priority Data

Sep. 23, 1975 [JP] Japan ................................ 50-115160

[51] Int. Cl.$^3$ .............................................. C07C 51/16
[52] U.S. Cl. ..................................................... 562/412
[58] Field of Search ....................... 260/523 A, 524 R; 562/412

[56] References Cited

U.S. PATENT DOCUMENTS

| | | | |
|---|---|---|---|
| 3,637,829 | 1/1972 | Kerr | 260/523 A |
| 3,683,017 | 8/1972 | Ager | 260/524 R |

Primary Examiner—Alan Siegel
Attorney, Agent, or Firm—Armstrong, Nikaido, Marmelstein & Kubovcik

[57] ABSTRACT

Terephthalic acid having a purity of 99% or more can be produced in a yield of 95% by mole or more by oxidizing p-tolualdehyde or a mixture of p-tolualdehyde and p-toluic acid with molecular oxygen in a solvent in the presence of a cobalt salt catalyst under the conditions that (1) a Co/solvent ratio is 0.05 to 0.70% by weight and (2) a toluic acid/Co ratio is 0.1 to 3.0 moles/gram atom, without using either a promoter or an oxidation accelerator.

8 Claims, No Drawings

PROCESS FOR PRODUCING TEREPHTHALIC ACID

The present invention relates to a process for producing terephthalic acid by oxidizing p-tolualdehyde or a mixture of p-tolualdehyde and p-toluic acid. More particularly, the invention pertains to a process for producing terephthalic acid having a high quality in a high yield by oxidizing p-tolualdehyde or a mixture of p-tolualdehyde and p-toluic acid with molecular oxygen in the presence of a small amount of a cobalt salt catalyst.

Terephthalic acid is usually produced from p-xylene, benzoic acid or phthalic acid on a commercial scale, and is an important compound as a raw material for polyesters. In the oxidation of p-xylene in the presence of a low concentration of a heavy metal salt catalyst, it is easy to convert one of methyl groups of xylene into carboxyl group but it is difficult to convert the methyl group of the p-toluic acid formed into carboxyl group at a practical velocity. As a process for producing terephthalic acid by the oxidation of p-xylene, therefore, there have been proposed a process which comprises using a high concentration of a cobalt salt catalyst, as disclosed in U.S. Pat. No. 3,334,135, a process which comprises using a bromine compound as a promoter, as disclosed in Japanese Patent Kokoku (Post-Exam. Publn.) No. 2,666/59, and a process which comprises using a compound such as methyl ethyl ketone, acetaldehyde or paraaldehyde as an oxidation accelerator, as disclosed in Japanese Patent Kokoku (Post-Exam. Publn.) Nos. 21,773/65, 24,180/65 and 13,856/65.

However, the above-mentioned processes have respectively defects. Thus, the process which comprises using a high concentration of a cobalt salt catalyst have defects in that the reaction velocity is low and it is necessary to recover the catalyst. Also, the process which comprises using a bromine compound as a promoter shows a high reaction velocity and is used in the production of terephthalic acid on a commercial scale, but corrosion resistant and expensive materials must be used for the apparatus owing to the severe corrosion thereof. Further, the process which comprises using an oxidation accelerator such as methyl ethyl ketone, acetaldehyde or paraaldehyde may be carried out under mild reaction conditions, but is not economical in that the oxidation accelerator is consumed.

In the production of terephthalic acid by oxidizing p-xylene, p-xylene is successively oxidized as follows:

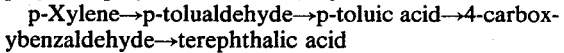

Therefore, any one of p-tolualdehyde, p-toluic acid and 4-carboxybenzaldehyde can be converted finally into terephthalic acid by oxidation according to a similar process to the oxidation of p-xylene. Thus, any one of p-tolualdehyde, p-toluic acid and 4-carboxybenzaldehyde can be a starting material for the production of terephthalic acid. Since a process for producing p-tolualdehyde from toluene and carbon monoxide by Gattermann-Koch reaction has been developed, however, a process for producing terephthalic acid from p-tolualdehyde or a mixture of p-tolualdehyde and p-toluic acid which can be easily derived from p-xylene or p-tolualdehyde, etc. has become important.

As a result of extensive studies to produce terephthalic acid in such a high yield and such a high quality as attained by the production of terephthalic acid by oxidation of p-xylene, that is, in a yield of 95% by mole or more and a purity of 99% or more by oxidizing p-tolualdehyde or a mixture of p-tolualdehyde and p-toluic acid with molecular oxygen without using a high concentration of a cobalt salt catalyst and without using either a promoter or an oxidation accelerator, the present inventors have now completed the process of the present invention. According to the present invention, there is provided a process for producing terephthalic acid which comprises oxidizing p-tolualdehyde or a mixture of p-tolualdehyde and p-toluic acid with molecular oxygen in a lower aliphatic monocarboxylic acid solvent in the presence of a cobalt salt catalyst, characterized by charging p-tolualdehyde or the mixture of p-tolualdehyde and p-toluic acid continuously into a complete mixing type reactor and reacting them under the conditions that (1) the cobalt salt catalyst is present in the reaction solution in an amount of 0.05 to 0.70% by weight as a metallic cobalt based on the weight of the solvent and (2) p-toluic acid is present in the reaction solution in an amount of 0.1 to 3.0 moles per gram atom of the metallic cobalt contained in the cobalt salt catalyst.

The p-tolualdehyde used as a starting material in the process of the present invention may be produced from toluene and carbon monoxide by the use of hydrogen fluoride-boron fluoride ($HF-BF_3$) or hydrogen chloride-aluminum chloride ($HCl-AlCl_3$) as a catalyst according to Gattermann-Koch reaction or may be produced by any other processes. Also, the p-toluic acid used as a starting material in the process of the present invention may be produced by, for example, oxidation of p-xylene or p-tolualdehyde.

As for the purity of p-tolualdehyde or a mixture of p-tolualdehyde and p-toluic acid, they may contain such an amount of isomers as is allowable in the product so long as they do not contain any inhibitor for the oxidation reaction, such as, for example, p-cresol. For example, p-tolualdehyde produced from toluene and carbon monoxide by the use of a hydrogen fluoride-boron fluoride catalyst is a mixture of about 95% of p-tolualdehyde and about 5% of o-tolualdehyde, and is purified by a usual purification method such as distillation or crystallization to obtain p-tolualdehyde having such a purity as required for the starting material for terephthalic acid, and can be used as a particularly preferable starting material in the process of the present invention. When a mixture of p-tolualdehyde and p-toluic acid is used as a starting material, up to 90% by weight of p-toluic acid based on the weight of the mixture may be used.

The cobalt salts used as a catalyst in the process of the present invention are inorganic salts such as cobalt carbonate and monocarboxylic acid salts such as cobalt acetate, cobalt propionate, cobalt butyrate, cobalt valerate or cobalt toluate, and may be used alone or as a mixture thereof.

The metallic cobalt concentration in the reaction solution is very important in the process of the present invention, and must be 0.05 to 0.70% by weight based on the weight of the solvent. If the metallic cobalt concentration is beyond the range, the following disadvantages are brought about:

(a) If the metallic cobalt concentration is less than 0.05% by weight and a molar ratio of p-toluic acid present in the reaction solution as starting material or as a reaction intermediate to metallic cobalt (hereinafter referred to as "toluic acid/cobalt") is less than 0.1, the reaction velocity per unit volume of the solvent is low.

(b) If the metallic cobalt concentration is less than 0.05% by weight and $0.1 \leq$ toluic acid/cobalt $\leq 3.0$, the reaction velocity per unit volume of the solvent is also low, and it is lacking in practical use.

(c) If the metallic cobalt concentration is less than 0.05% by weight and toluic acid/cobalt is more than 3.0, p-tolualdehyde is very easily oxidized into p-toluic acid but the formation reaction velocity of terephthalic acid from p-toluic acid is low and it is also lacking in practical use.

(d) If the metallic cobalt concentration exceeds 0.70% by weight and toluic acid/cobalt is less than 0.1, the reaction velocity is very low and is not satisfactory for the production of terephthalic acid on a commercial scale.

(e) If the metallic cobalt concentration exceeds 0.70% by weight and toluic acid/cobalt is 0.1 or more, the reaction velocity per unit volume of the solvent is high but p-toluic acid and 4-carboxybenzaldehyde as reaction intermediates are contained in the terephthalic acid thus obtained, and terephthalic acid of a high purity can not be obtained. Further, the amount of cobalt metal occluded or contained in the terephthalic acid is large and a heavy burden is imposed on the purification step of terephthalic acid.

In the process of the present invention, the amount of p-toluic acid present in the reaction mixture has a large influence upon the reaction velocity and the quality of the resulting terephthalic acid in connection with the amount of metallic cobalt, and the condition of $0.1 \leq$ toluic acid/cobalt $\leq 3.0$ must be maintained during the reaction. If toluic acid/cobalt is less than 0.1, the reaction velocity of oxidation of p-toluic acid becomes very slow. Also, if toluic acid/cobalt is more than 3.0, the reaction velocity of oxidation of p-toluic acid decreases and as a result, the purity of the resulting terephthalic acid is remarkably reduced.

The amount of p-toluic acid present in the reaction solution can be controlled by regulating the residence time of the reaction mixture in the reactor and/or the reaction temperature. If the residence time of the reaction mixture in the reactor is long, the amount of p-toluic acid decreases. Also, if the reaction temperature is elevated within a reaction temperature range suitable for the oxidation reaction, the amount of p-toluic acid likewise decreases. The preferable residence time for the process of the present invention is 70 to 180 minutes.

p-Tolualdehyde is oxidized into p-toluic acid in a comparatively short period of time, and oxidation of p-toluic acid into terephthalic acid also proceeds simultaneously while p-tolualdehyde is present together with p-toluic acid. After the total amount of p-tolualdehyde has been converted into p-toluic acid, however, the oxidation reaction velocity of p-toluic acid into terephthalic acid becomes very slow and it is impossible to convert p-toluic acid completely into terephthalic acid. In order to convert p-toluic acid completely into terephthalic acid, therefore, p-tolualdehyde must be always present in the reaction mixture. In the process of the present invention, the above-mentioned condition can be satisfied since p-tolualdehyde or a mixture of p-tolualdehyde and p-toluic acid is continuously charged into a complete mixing type reactor. Back mixing is sufficiently effected in the complete mixing type reactor. Therefore, the starting material containing p-tolualdehyde as charged continuously is thoroughly mixed with the reaction solution in the reactor in a short period of time to form a uniform composition. Thus, p-tolualdehyde is always present in the reaction solution and the concentration of p-tolualdehyde is maintained at a definite value.

The reaction temperature suitable for the practice of the present invention is 50° to 150° C., and preferably 100° to 140° C. If the reaction temperature is lower than 50° C., the reaction velocity is low. If the reaction temperature is higher than 150° C., the cobalt salts showing a catalytic activity in the oxidation reaction are inactivated and it is impossible to obtain terephthalic acid of a high quality in a high yield in a short period of time.

The term "molecular oxygen" used in the present specification means oxygen gas or a mixture of oxygen gas and an inert gas such as nitrogen gas. Air is generally used as molecular oxygen. If the partial pressure of oxygen is 0.1 to 10 kg/cm$^2$ (absolute), the oxidation reaction proceeds smoothly. If the partial pressure of oxygen is less than 0.1 kg/cm$^2$, it is impossible to effect a steady oxidation reaction. If the partial pressure of oxygen exceeds 10 kg/cm$^2$, it is not a great hindrance to the reaction but it is not economical.

The solvent used in the present invention is a lower aliphatic monocarboxylic acid such as acetic acid, propionic acid, butyric acid or valeric acid. Acetic acid is particularly preferred as the solvent. The acetic acid used usually has a purity of 90 to 100%. (The remainder is water.) Acetic acid having a purity of 95% is particularly preferable in that a load in the acetic acid purification step is minimized. It is possible to use acetic acid having a purity of less than 90% as the solvent, but is not desirable since the decomposition of a highly active cobalt complex having a catalytic activity occurs if the amount of water contained in the reaction system is more than 10%.

As a method for charging p-tolualdehyde or a mixture of p-tolualdehyde and p-toluic acid into a reactor, there are various embodiments such as a method which comprises dissolving p-tolualdehyde or the mixture in the solvent and then charging the resulting solution into the reactor, or a method which comprises charging the starting material or starting materials and the solvent separately into the reactor. When the starting material or starting materials are dissolved in the solvent and the resulting solution is then charged into a reactor, the concentration of p-tolualdehyde or the sum concentration of p-tolualdehyde and p-toluic acid is suitably 10 to 30% by weight. If the concentration is less than 10% by weight, it is lacking in practicability from various viewpoints. If the concentration exceeds 30% by weight, the handling of a slurry containing the resulting terephthalic acid becomes difficult.

The product solution obtained by the process of the present invention is a slurry containing crystalline terephthalic acid. The slurry may be filtered and the thus obtained crystals may be washed with acetic acid and/or water and then dried to obtain terephthalic acid.

According to the process of the present invention, terephthalic acid can be produced from p-tolualdehyde or a mixture of p-tolualdehyde and p-toluic acid by the use of a low concentration of a cobalt salt catalyst without using any promoter or oxidation accelerator, in contrast with a prior art process for oxidizing p-xylene into terephthalic acid.

The greater part of terephthalic acid crystallizes out almost simultaneously with its formation owing to its low solubility in solvents, and p-toluic acid and 4-carboxybenzaldehyde are occluded and contained thereby. When the composition of the reaction solution varies according to the place in the reactor or when the composition of the reaction solution varies with the lapse of time, the amount of p-toluic acid and 4-carboxybenzaldehyde occluded and contained in the crystalline terephthalic acid varies with the lapse of time. If a complete mixing type reactor is used as described above, however, the composition of the reaction solution is kept constant all the time. Therefore, terephthalic acid having a constant purity of 99% or more (an acid value of about 672 or more) can be produced in a yield of 95% by mole or more.

The following examples illustrate the process of the present invention in more detail.

EXAMPLE 1

As a reactor was used a 400 ml-volume complete mixing type reactor equipped with a stirrer, a peephole, a jacket for temperature control, a nozzle for blowing air, an exit for an exhaust gas, an inlet for a stock solution and an exit for withdrawing the product solution.

A stock solution comsisting of 200 g of p-tolualdehyde, 10 g of cobalt acetate and 1000 g of glacial acetic acid was charged into the reactor at a rate of 270 ml/hr. The reaction solution was thoroughly mixed by the stirrer and oxygen was blown while the temperature of the inside of the reactor was maintained at 130° C. The reaction was carried out at a reaction pressure of 3 kg/cm$^2$. The vapor phase portion was withdrawn from the reaction system at a rate of 5 l/hr to prevent the accumulation of the gas produced. The product slurry was then withdrawn at such a rate as the quantity of the contents of the reactor might be kept constant. The acid value, yield and purity of the resulting terephthalic acid were as shown in Table 1.

EXAMPLE 2

All the same operations as in Example 1 were carried out except that the rate at which the stock solution was charged was 200 ml/hr. The results obtained were as shown in Table 1.

EXAMPLE 3

All the same operations as in Example 1 were carried out except that the rate at which the stock solution was charged was 160 ml/hr. The results obtained were as shown in Table 1.

Table 1

|  | Cobalt concentration (based on the weight of solvent) (% by weight) | Average residence time (min.) | Toluic acid/* cobalt | Acid** value | Yield of terephthalic acid (% by mole) | Purity of terephthalic acid (%) |
| --- | --- | --- | --- | --- | --- | --- |
| Example 1 | 0.24 | 90 | 1.25 | 672 | 95.0 | 99.0 |
| Example 2 | 0.24 | 120 | 1.05 | 674 | 95.1 | 99.4 |
| Example 3 | 0.24 | 150 | 0.55 | 675 | 97.3 | 99.5 |

*The amount of p-toluic acid was obtained by collecting the reaction solution and subjecting it to gas chromatography.
**Acid value is a criterion for the purity of terephthalic acid. Pure terephthalic acid has an acid value of 675.5.

COMPARATIVE EXAMPLES 1, 2 AND 3

All the same operations as in Example 1 were carried out except that the amount of the stock solution charged was as shown in Table 2. The acid value, yield and purity of the resulting terephthalic acid were as shown in Table 2.

Table 2

|  | Cobalt concentration (based on the weight of solvent) (% by weight) | Amount of stock solution charged (ml/hr) | Average residence time (min.) | Toluic acid/ cobalt | Acid value | Yield of terephthalic acid (% by mole) | Purity of terephthalic acid (%) |
| --- | --- | --- | --- | --- | --- | --- | --- |
| Comparative Example 1 | 0.24 | 400 | 60 | 4.90 | 664 | 81.9 | 95.6 |
| Comparative Example 2 | 0.24 | 533 | 45 | 6.70 | 660 | 75.3 | 94.3 |
| Comparative Example 3 | 0.24 | 800 | 30 | 11.1 | 652 | 71.7 | 92.2 |

COMPARATIVE EXAMPLE 4

Into an autoclave were charged 100 g of glacial acetic acid, 20 g of p-tolualdehyde and 1 g of cobalt acetate (cobalt concentration 0.24% by weight based on the weight of the solution). The reaction was carried out at a temperature of 130° C. and an oxygen pressure of 3 kg/cm$^2$ for 2 hours according to a batch process. The value of toluic acid/cobalt was about 20. As a result, the conversion of p-tolualdehyde was 99%, the yields of p-toluic acid and terephthalic acid were 55.4% by mole and 39.8% by mole, respectively, and the purity of terephthalic acid was 79.0%. Also, the acid value of terephthalic acid was 607.

EXAMPLE 4

All the same operations as in Example 1 were carried out except that a stock solution consisting of 1000 g of glacial acetic acid, 108 g of p-tolualdehyde, 122 g of p-toluic acid and 10 g of cobalt acetate (cobalt concentration 0.24% by weight based on the weight of the solvent) was charged into the reactor at a rate of 160 ml/hr. The value of toluic acid/cobalt in the reaction solution at a steady state was 1.34 and the average residence time of the reaction solution was 160 minutes. As a result, terephthalic acid having an acid value of 672 and a purity of 99.1% was obtained in a yield of 95.1% by mole.

COMPARATIVE EXAMPLE 5

All the same operations as in Example 1 were carried out except that the amount of cobalt acetate was 50 g (cobalt concentration 1.2% by weight based on the weight of the solvent). The value of toluic acid/cobalt in the reaction solution at a steady state was 0.38 and the average residence time of the reaction solution was 90 minutes. As a result, terephthalic acid having an acid value of 669 and a purity of 97.7% was obtained in a yield of 91.5% by mole.

EXAMPLE 5

A stock solution consisting of 1000 g of glacial acetic acid, 26 g of cobalt butyrate (cobalt concentration 0.50% by weight based on the weight of the solvent) and 200 g of p-tolualdehyde was charged into the same reactor as that used in Example 1 at a rate of 160 ml/hr. The reaction solution was throughly mixed by the stirrer and air was blown therein while the temperature of the inside of the reactor was maintained at 115° C. The reaction was carried out at a reaction pressure of 30 kg/cm$^2$ (i.e. a partial pressure of oxygen of 6 kg/cm$^2$). The vapor phase portion was withdrawn from the reaction system at a rate of 80 l/hr. The value of toluic acid/cobalt in the reaction solution at a steady state was 1.10 and the average residence time of the reaction solution was 150 minutes. As a result, terephthalic acid having an acid value of 671 and a purity of 99.2% was obtained in a yield of 95.0% by mole.

What is claimed is:

1. A process for producing terephthalic acid which comprises oxidizing p-tolualdehyde or a mixture of p-tolualdehyde and p-toluic acid with molecular oxygen in a lower aliphatic monocarboxylic acid solvent in the presence of a cobalt salt catalyst selected from the group consisting of cobalt carbonate, cobalt acetate, cobalt propionate, cobalt butyrate, cobalt valerate, cobalt toluate and a mixture thereof the process being characterized by charging p-tolualdehyde or the mixture of p-tolualdehyde and p-toluic acid continuously into a complete mixing type reactor and reacting them under the conditions that (1) the cobalt salt catalyst is present in the reaction solution in an amount of 0.05 to 0.70% by weight as a metallic cobalt based on the weight of the solvent and (2) p-toluic acid is present in the reaction solution during the reaction in an amount of 0.1 to 3.0 moles per gram atom of the metallic cobalt contained in the cobalt salt catalyst.

2. A process according to claim 1, wherein the residence time of the reaction solution in the reactor is 70 to 180 minutes.

3. A process according to claim 1, wherein the reaction is carried out at a temperature of 50° to 150° C.

4. A process according to claim 1, wherein said molecular oxygen is air.

5. A process according to claim 1, wherein the pressure of oxygen is 0.1 to 10 kg/cm$^2$ (absolute).

6. A process according to claim 1, wherein said lower aliphatic monocarboxylic acid solvent is acetic acid.

7. A process according to claim 6, wherein said acetic acid has a purity of 90 to 100%.

8. A process according to claim 1, wherein the mixture of p-tolualdehyde and p-toluic acid contains not more than 90% by weight of p-toluic acid based on the weight of the mixture.

* * * * *